United States Patent [19]

Fellus

[11] 4,197,851

[45] Apr. 15, 1980

[54] APPARATUS FOR EMITTING HIGH-FREQUENCY ELECTROMAGNETIC WAVES

[76] Inventor: Victor M. Fellus, 24, rue Joseph Bertrand, 78220 Viroflay, France

[21] Appl. No.: 872,959

[22] Filed: Jan. 27, 1978

[30] Foreign Application Priority Data

Apr. 14, 1977 [FR] France .................... 77 11191

[51] Int. Cl.² .............................................. A61N 1/40
[52] U.S. Cl. .................................... 128/422; 128/798
[58] Field of Search ................. 128/404, 405, 416, 421, 128/422

[56] References Cited

U.S. PATENT DOCUMENTS

| | | | |
|---|---|---|---|
| 1,889,271 | 11/1932 | Zerne | 128/416 |
| 2,109,726 | 3/1938 | Huppert | 128/405 |
| 2,181,535 | 5/1955 | Milinowski | 128/422 |
| 2,838,672 | 6/1958 | Paust | 128/422 |
| 3,662,757 | 5/1972 | Blackett | 128/416 |

FOREIGN PATENT DOCUMENTS

2236521  2/1975  France ..................................... 128/404

OTHER PUBLICATIONS

General Electric X-Ray Corporation Publication Number 7P-158, 4 pp.

*Primary Examiner*—Willaim E. Kamm
*Attorney, Agent, or Firm*—Brisebois & Kruger

[57] ABSTRACT

Apparatus for emitting high frequency electromagnetic waves comprises a low-voltage power supply, an emitter and an antenna comprising at least one conductor on a thin flexible insulating support and including a length of conductive material formed into a pattern and having interconnected ends in the region of which the conductor is connected to the output of the emitter by a single connector. This not only enables the whole antenna to be flexible so that it can be applied to areas difficult of access, e.g. parts of the human body and even be rolled into a tube for insertion in a body cavity, or wrapped around a limb, for example, but the emitter operates at a voltage of less than 50 volts, the antenna is athermic and the apparatus is significantly small. This is in contradistraction to the high voltage, bulky equipment hitherto used for therapeutic treatment of the body of a patient, both human and animal. The antenna may be associated with current-emitting electrodes and such current may be emitted alternately or simultaneously with the emission from the antenna. The emitter may be caused to emit trains of waves at frequencies between 1 HZ and 100 MHz, and the energy strength may be less than 100 MW per square centimeter.

11 Claims, 6 Drawing Figures

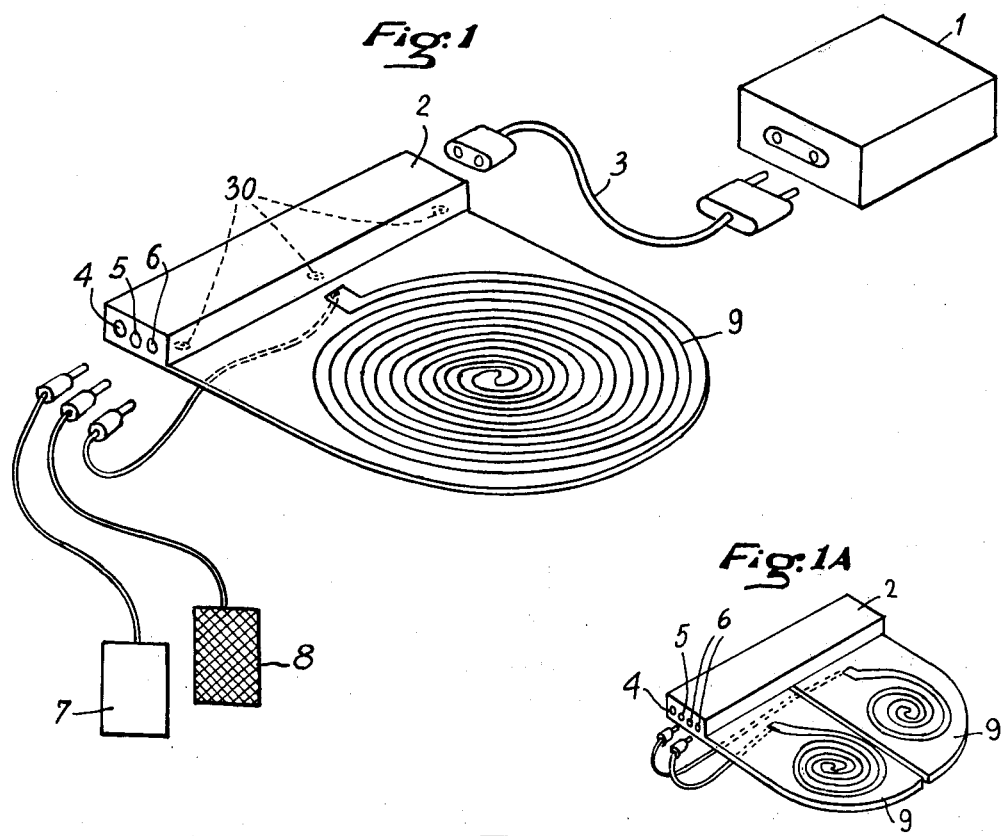

APPARATUS FOR EMITTING HIGH-FREQUENCY ELECTROMAGNETIC WAVES

BACKGROUND OF THE INVENTION

The present invention relates to apparatus which emits high-frequency electromagnetic waves, and in particular to an antenna and antenna feed device which allows the energy emitted by the antenna to be accurately adjusted in respect of power and position.

Hereinafter, the energy will in all cases be measured at the point of use. If for example what are involved are medical applications of the apparatus, the energy measured will be that received at the skin of the patient in the area to be treated.

Such devices can be applied in very many fields and in particular in all those where research, development and industry require the application of an electromagnetic field under extremely accurate conditions as regards location and/or power. In prior art devices, when it is desired to produce a strong electromagnetic field over a small area, or a concentrated field, or one which is distributed in a precise pattern, or again when it is desired to shift the field continuously or discreetly, recourse is usually had to very bulky and generally somewhat inaccurate apparatus. However, the bulk considerably restricts possible uses and the general trend towards miniaturisation poses problems which cannot be solved simply by a change of scale. It is clear that there are techniques, such as those used in astronautics, which are relying to a greater and greater extent on equipment which is extremely light and extremely versatile in production and in use. If for example it is desired to produce an electromagnetic field in areas which are difficult of access or on objects which are small in size, the use of conventional antennas soon presents problems.

Furthermore, in accordance with the desiderata upon which the present invention is based, the apparatus should be able to emit purely electrical fields or currents, at the same time as or alternately with trains of electromagnetic waves.

This would enable the electromagnetic fields and the electrical currents to be separated and in particular it enables thermal phenomena, which are often a nuisance, to be controlled, as will be seen below.

Also a further object of the invention is to provide such apparatus particularly suitable for biological applications, and in particular medical or veterinary applications. It should in fact be able to be used "in situ", that is to say in the immediate vicinity of the area to be treated, or possibly in an implanted position.

There are many kinds of apparatus in the prior art for generating electrical currents or for emitting magnetic, electrical or electromagnetic fields which operate in fairly varied frequency bands. Such pieces of apparatus may operate either as current generators or as field emitters and may do so for either temporary or long-term use on the premises of the person giving treatment or by the patient's bed. They may operate continuously or intermittently. Such pieces of apparatus are more bulky or less transportable the higher the level of the energy given out and becuase high voltages are normally used. The therapeutic effects are generally considered to depend on the amount of energy received in the tissues to be treated and on certain other physical, and especially thermal, parameters.

Such pieces of apparatus can only be used where there is a qualified medical staff and if the patient is brought to the place of use, which often involves frequent and painful journeys. Because of this, there are numerous occasions on which people fail to take treatment which could bring about a significant reduction in the healing period, for example in cases of immobilisation in plaster following bone fractures.

To avoid any confusion, the basic vocabulary will be reviewed taking the example of biological and medical applications as a basis. When use is made of current, at least two electrodes are employed, these electrodes being applied to the patient, who becomes a conductive element in the circuit. This chiefly produces various physical and chemical effects (a thermal Joule effect, inophoresis which provides for the passage of ions through the tissues, etc.) and nerve effects (a motor exciting effect). The currents used are often termed galvanic (continuous) or faradic (pulsed). Use has also been made in the prior art, of what have for long been known as short waves. What this involves is creating a capacitive, and thus purely electrical, field by means of at least two plates or electrodes which are placed on either side of the patient, generally at a distance from him or her, the patient becoming a di-electric element. The di-electric losses then give rise to heating. Operations often take place with only one electrode or plate with the patient forming an earth. This may result in a sparking phenomenon between the electrode and the patient. In none of these short wave techniques is there any attempt to achieve a magnetic field effect.

Use has also been made of apparatus for emitting electromagnetic fields, which usually relies on induction coils. However, the present day trend is to use higher and higher energy levels and in particular high voltages, which results in vast pieces of equipment and makes them difficult to use for many applications, as was stated above.

SUMMARY OF THE INVENTION

To achieve the above and other objects, the invention provides apparatus for emitting high frequency electromagnetic waves, comprising an emitter and an antenna, wherein said antenna is formed by at least one conductor on a thin insulating support.

The invention furthermore proposes to utilise voltages of less than 50 V and of energies of less than 100 mW per cm$^2$ of receiving surface and this enables harmful thermal effects to be avoided, bulk to be considerably reduced, and high-frequency emitting antennas to be used which, while still being very closely positionable to the patient, do not give rise to the normal dangers, such as sparking for example which would convert the apparatus into an electrical lancet, as may occur with present day high-energy apparatus. Thus, "antenna" as used herein means a device which is not intended to set up a flow of current between the apparatus and the patient, as is the case with electrodes which operate in direct electrical contact, but a device which has no electrical contact with the patient and which generally operates on its own (unlike the plates or electrodes used as parts of a capacitor) and which is fed by only one conductor (unlike inductance coils).

Studies have now shown that many elementary crystalline structures exhibit behaviour which is extremely interesting from the technical and scientific points of view when they are subjected to electromagnetic fields. This is true both of liquid crystals and of many other structures and in particular of living matter.

It is apparent from these studies that minimal energies, i.e. energies of relatively low level, are able to act in an optimum fashion if they are applied with the field carefully localised. Experience has shown that in certain cases energies of the order of a few mW/cm$^2$ or even a few $\mu$W/cm$^2$ have significant effects. The advantage of the devices according to the present invention is that, as has been emphasised, they do not involve the use of bulky equipment which is difficult to transport. In particular they are suitable for use under conditions where this would have been difficult hitherto, by virtue of the fact that the antenna can be introduced into confined areas or areas difficult to get at and by virtue of the fact that they emit electromagnetic fields in a region which is defined geometrically with great accuracy, the emitted power being distributed or concentrated in an equally accurate manner in the area which it is desired to subject to the field so emitted. It is found that in very many applications very low energy levels are all that are needed, whereas with conventional apparatus, where the field is difficult to concentrate because of the large size of the apparatus and the antenna, it is necessary to have recourse to high energy levels, which means a considerable amount of waste. The need to maintain a distance from the patient, in particular because high voltage is used, likewise increases innacuracies in use and in the measurement of the amount of energy received by the surface to be treated.

It is easy in accordance with the invention to achieve a very accurate distribution with all energies of less than 100 mW/cm$^2$, which is adequate for very many applications.

By selecting in particular the shape of the emitting antenna and the method of supplying it, it is open to the man skilled in the art to apportion, and possibly shift, the field while at the same time regulating its density in the working area.

In medical use, energy levels of less than 100, and even of less than 10 mW/cm$^2$ avoid, in particular, the familiar harmful effects which are found with certain prior art apparatus. Experience has also shown that the form of the emissions (contour of field, frequency, amplitude) has an appreciable effect on the effectiveness or dangerousness of the devices. Furthermore, the apparatus according to the invention, unlike prior art apparatus, allow treatment to be given simultaneously at high frequency and by other technical means, such as ionophoresis, motor exciting currents, interferential currents, or ultrasonics. The invention lies primarily in providing antennas of generally small dimensions which are preferably mounted on an easily handled support to allow, in a miniaturisation context, an electromagnetic field to be emitted with precision, as defined above, in particular by reason of the fact that the antenna is in practice in mechanical contact with the patient although electrically isolated for him or her. For this use is made, in a preferred embodiment of the invention, of antennas which are produced by printing conductive material on a flexible insulating surface. In particular this enables the antenna to be placed on all kinds of support and in particular in areas which are difficult of access, such as inside a cavity or in the interstices of a composite material. What is more, it makes it possible to obtain, on the same support or different supports, a lay-out comprising a plurality of antennas which may or may not be interengaged and which, when fed in sequence for example, allow the field to be shifted.

In the medical applications which are alluded to above, the results achieved have proved particularly effective and it can be conceded that current research indicates that a major factor in the therapeutic effect of the treatment is the molecular re-ordering in the electromagnetic field. It should also be emphasised, that, although it is possible to envisage having one or more electromagnetically emitting high-frequency antennas and one or more electrodes on the same or different supports, the function performed by the electrode is known per se from the prior art, where extensive use is made of the application of current by means of plates, grids, bars and the like.

The following example will be restricted, to serve as an illustration, to a small and simple apparatus which both allows an electromagnetic field to be emitted by means of an antenna and an electrical current to be emitted by means of two electrodes. It is clear that, as has just been emphasised, the invention has to do chiefly with the emission of a high-frequency electromagnetic field by the antenna and that its supply device is also able, if required, to supply electrodes with electrical signals and thus to allow the subsequent thermal effects to be very strictly controlled.

BRIEF DESCRIPTION OF THE DRAWINGS

In order that the technical features and the advantages of the present invention may be better understood, one embodiment thereof will now be described, it being understood that this embodiment is not limiting either in respect of its construction or in respect of its possible applications. Accordingly, reference will now be be made to the accompanying drawings in which:

FIG. 1 shows a schematic general view of an apparatus according to the invention, FIG. 1A is a diagrammatic schematic view of a modification, FIG. 2 shows a block diagram of a circuit according to the invention, FIG. 3 shows a diagram of the signal emitted by means of the circuit of FIG. 2.

DETAILED DESCRIPTION OF PREFERRED EMBODIMENTS

Figure 1B:
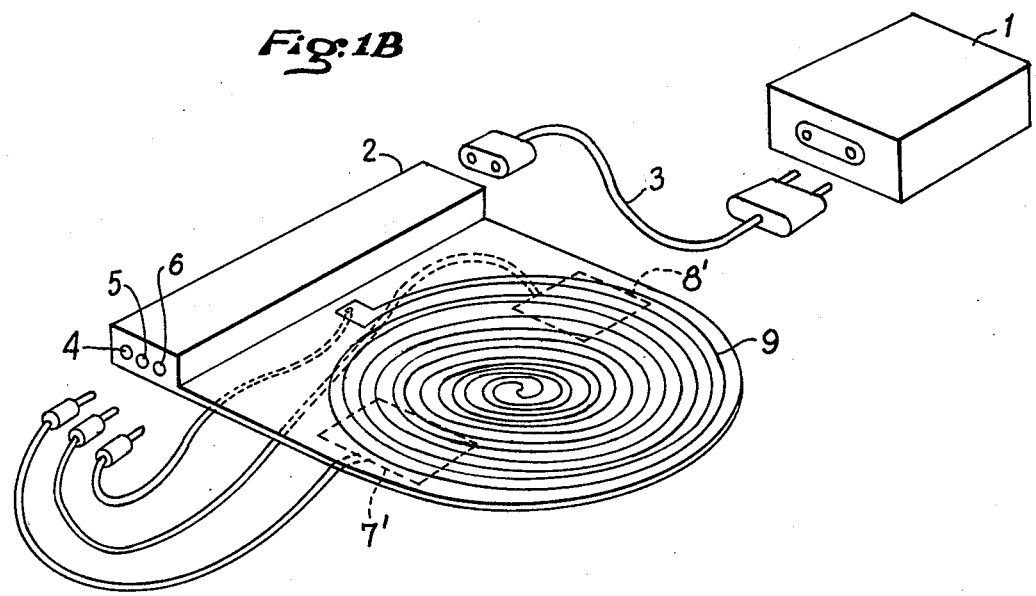
FIG. 1B shows schematically an alternative embodiment in which the electrodes are mounted on the antenna support.

The apparatus according to the invention as shown in FIG. 1 is formed in essence by a low voltage power supply schematically shown by a housing 1 and which may be a battery, transformer or the like, said power supply being connected to a main housing 2 by means of a cable 3. The housing 2 will be described in detail at a later stage. The housing has three output terminals: two terminals 4 and 5 for the connection of electrodes 7 and 8, and one terminal 6 for the connection of an antenna 9. The electrodes 7 and 8 may be of widely varying kinds and are used to apply an electric current to the patient to be treated. They may be formed by plates, tapes, grids, sheets, or even needles so that they may be capable of being implanted if required or necessary. As will be seen, one of the electrodes is earthed and the other is live. To place the electrodes in position, any conventional method may be used, such as a conductive paste which provides good electrical transmission.

The antenna 9 is preferably formed by a flexible insulating sheet on which is printed a conductive circuit forming the antenna; use could also be made of a wire bonded to the sheet. This flexible sheet is preferably used in a protective pouch (not shown) which is flexible and insulating and which avoids surface phenomena arising from contact with the patient's skin. It may also be insulated by a lacquer or a film.

This kind of flexible antenna according to the invention is greatly applied directly to the area to be treated of a patient's body and the electromagnetic field produced thereby is without significant thermal effects on the patient's body. The man skilled in the art can select the form of the printed pattern forming the antenna and this allows for the distribution of the field to be accurately determined and in particular the energy density. In FIG. 1, the pattern is formed by two spirals which are joined at both ends, the outer end being connected to 6 by means of a conductive wire and a plug. It is particularly useful for the antenna to be interchangeable, i.e. for the supporting sheet to be detachably secured to the housing 2 by any suitable means, such as adhesive, press fasteners shown diagrammatically at 30, plug-in connections such as plug-in edge connectors well known in the art, or the like. A plug-in edge connection for example may replace the system consisting of the terminal 6 and the wire shown in FIG. 1 but this has not been illustrated since it will be apparent to those skilled in the art. The interchangeable nature of the antenna makes it possible for the form of antenna to be changed and in particular for operations to take place under completely aseptic conditions when there is a change of patient. As will be seen, the housing 2 may be of sufficiently small volume to enable the assembly comprising the housing 2 and the antenna 9 to be positioned easily in areas which are difficult of access and in particular on the patient himself underneath a dressing, bandage, splint, plaster or the like.

The supply device may be conventional. Below, a description will be given of a type of supply which is particularly suited to the case illustrated by the present example.

The principle on which the housing 2 operates is as follows referring to FIGS. 2 and 3. The power-supply 10 of FIG. 2, which would be fitted in housing 1 of FIG. 1, is followed by a combination 11, 12, 13 which would be fitted in housing 2. The device shown at 11 is a multivibrator the signals from which are shaped by a shaper 12. The electrical signals are collected at terminal 13, and at a high-frequency stage shown at 14, there are produced signals which are transmitted at terminal 15 to the antenna 9.

If the HF signals are transmitted in regular successive trains (first waveform in FIG. 3), as they are in a preferred embodiment of the invention, the electrical signals emitted at 13 may be of the type shown at E1, i.e. in the intervals between the successive HF wave trains, or may be emitted simultaneously, as shown at F$_2$.

As regards the high frequency, operations take place for example at 27.125±0.125 MHz, which is covered by one of the bands set aside for high-frequency medical use.

The length of the HF wave trains may be of the order of 10 to 100 microseconds, and the repetition frequency of the successive trains may be of the order of 1 Hz to 100 MHz.

As regards the electrical signals, the voltage applied to the electrodes 7 and 8 is generally of the order of 3 to 10 volts and preferably of the order of 5 to 6 volts, the intensity of the current flowing in the part to be treated being very low.

Figure 4:
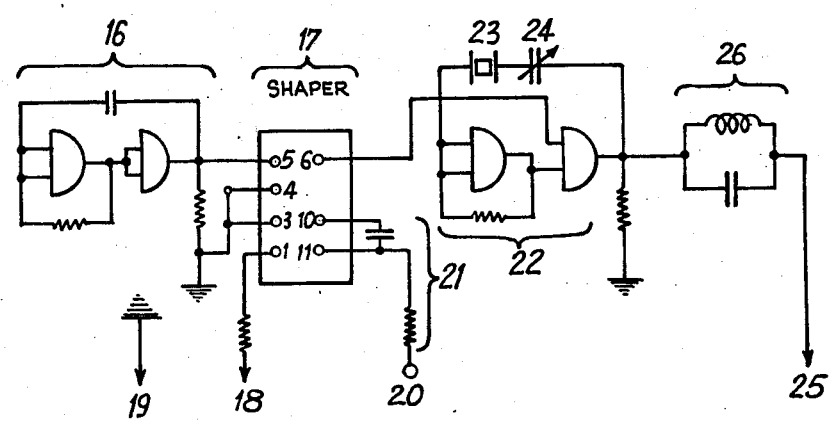
FIG. 4 shows an embodiment of the circuit of FIG. 2.

In FIG. 4 can be seen a detailed embodiment of the items in the block diagram of FIG. 2. The oscillator assembly 16 governs the repetition rate of the HF wave trains and the frequency of the electrical signals and is made up of conventional elements as shown by the conventional representations thereof. There are many integrated circuits which can be used as oscillators of this kind. The signals are transmitted to a device 17 to allow the HF and electrical signals to be shaped. The device 17 may be a 74, 121 integrated circuit (international coding; such an integrated circuit is made inter alia by Sescosem and Texas Instruments). At terminal 18 are received the electrical signals which, in association with the earth 19, represent the signals at terminals 4 and 5 of FIG. 1. At terminals 10. 11 of the 74,121 circuit is inserted an assembly 21 for regulating the length of the HF wave-trains or the electrical signals, 20 being connected to the power supply.

From terminal 6 of the 74,121 circuit are emitted signals which are passed to an HF emitter 22 which is quartz controlled by crystal 23 to the selected frequency set by capacitor 24. The HF wave trains are transmitted to the antenna at terminal 25 via an LC circuit 26 for matching to the antenna. If 16 corresponds to 11 (FIG. 2). 17 and 21 correspond to 12, and 22, 23, 24 and 26 correspond to 14. Terminals 18 and 19 correspond to 13, i.e. to 7 and 8 (FIG. 1), and terminal 25 corresponds to 15 (FIG. 2) and 6 (FIG. 1).

In FIG. 3, electrical pulses whose sign is opposite from the pulses shown in solid lines are shown in broken lines at E'2. This illustrates the possibility of emitting in all cases, be they E1, E2 or others, either positive going pulses, or negative going pulses, or alternating pulses.

In the present examples, the antennas will always be insulated from the patient by means of, for example, a simple lacquer with which they are coated or an insulating material sheath or pouch, whereas when electrodes are used the best possible electrical contact needs to be provided with the patient. When for example antennas and electrodes are printed on the same support, as shown for electrodes 7' and 8' in FIG. 1B they can be placed on either side of the support, which will allow the antennas when situated on the opposite side from the patient to be electrically insulated. It is clear that the man skilled in the art will be able to make any modifications. It is of course possible to use only one, common housing combining the circuit components contained in housings 1,2 either in situ on the antenna or separate from it. Furthermore, the electrodes may be located on the antenna support.

Different antennas on the same or different supports as shown in FIG. 1A may be fed simultaneously or in sequence to shift the field, in which latter case the emitter includes means indicated by the dashed lines 31 in FIG. 4, for energizing the antennas in sequence. It is of course possible to vary the strength of the field.

Certain specific and important medical and biological applications have been found and in particular those involving the use of very small antennas in particular regions, for example in acupuncture where the action of the acupuncture needle may be combined with electromagnetic emission, or even better, substituted for it.

The needle may for example be placed at the centre of the turns of the antenna either in isolation from it or in contact with it. It is equally possible not to use needles, small antennas being positioned at the position of the needle points normally used in acupuncture.

Due to their small dimensions, circuit housings such as 2 may in particular be fitted in situ on the antenna and its support, and in particular this will allow connections to be made very easily by press-fasteners such as 31, at least one of which is conductive. As was emphasised above, the form of the antenna support may be adapted to its intended use, for example by making it of cylindrical or conical shape or in the shape of the finger of a glove, to allow it to enter cavities.

As has been emphasised, it is possible, if desired, to associate electrodes with the electromagnetic field emitter to allow an electrical current to flow, the electrodes being in electrical contact with the skin of the patient and the antenna being insulated, for example by being printed on the other face of the support as described above.

It is also possible to make use, on supports of various forms, of antennas which are fed sequentially, as has been mentioned, and to create a moving field, for example by placing a series of antennas similar to that shown in FIG. 1 in a circle on a support in the shape of a disc. The field can be caused to travel round in steps, antenna by antenna, which allows treatment to be given to a large area such as the chest or face. Similarly, by placing a number of antennas along a longitudinal strip and feeding them in sequence, it is possible to treat the spinal column or any other elongated member. By rolling a long support provided with a plurality of antennas in a line into a cylinder, it is possible to obtain a field which travels round in steps, antenna by antenna, around limbs or inside a cavity for example. The man skilled in the art will thus be able to shape the antennas and their support and arrange to feed them simultaneously or in sequence as dictated by the medical or other applications for which they are used. An application has been found for such antennas in many other fields for example in the biological field for treating seeds.

Mention was made above of a frequency of 27.125 MHz. However, it appears that a relatively wide frequency band may be useful. In fact, if the example given is based on a frequency of 27.125 MHz, which is substantially equivalent to a wave-length of 11 m, this is only because this frequency is allotted to medical apparatus.

In fact, millimetric, centimetric, decimetric and meter wave-lengths all prove effective depending on the sphere of application, but are not currently used principally for statutory reasons. It is therefore necessary to make provision for it to be possible for apparatus according to the invention to be used, where international agreements permit, at frequencies other than those quoted in the example. Thus "high frequency" in the present text should be understood to mean this wide band of frequencies and the corresponding wave-lengths.

I claim:
1. Apparatus for emitting high-frequency electromagnetic waves, said apparatus comprising:
   a low-voltage power supply,
   a solid state circuit means for producing high-frequency, low-energy electromagnetic waves, said circuit means comprising an output which emits said high-frequency, low-energy electromagnetic waves, and an input,
   means connecting said input to said power supply,
   at least one antenna connected to the output of said circuit means, for producing a low energy high-frequency electromagnetic field without significant thermal effects in response to the waves produced by said circuit means,
   said antenna comprising at least one conductor on a support which is formed from an electrically insulating material applicable directly on the skin of a patient's body and formed to conform to the contour of the area of the body to which it is applied,
   said at least one conductor including a length of thin conductive material in a predetermined pattern on said support to apply the electromagnetic waves to the body.

2. Apparatus according to claim 1, and further comprising current-emitting electrodes situated on an insulating face of said support, and wherein said solid state circuit means includes means for supplying low-frequency electrical pulses to said current-emitting electrodes.

3. Apparatus according to claim 2, wherein said means for producing low-frequency electrical pulses comprises a multivibrator having an input connected to said power supply and an output, and a pulse shaping stage having an input connected to the output of the multivibrator, the pulse shaping stage having an output for supplying said current-emitting electrodes and a further output, and wherein said circuit means includes a high-frequency stage having an input which is connected to said further output of said pulse shaping stage, and an output connected to said antenna.

4. Apparatus according to claim 3, wherein said pulse shaping stage includes means for connecting said multivibrator alternately to the two outputs of said pulse shaping stage to alternately energize said current emitting electrodes and said antennas.

5. Apparatus according to claim 3 wherein said multivibrator comprises means for generating pulses to control said high frequency stage to emit trains of said electromagnetic waves at repetition frequencies of between 1 Hz and 100 MHz.

6. Apparatus according to claim 2, wherein said antenna conductor and said electrodes are in the form of circuits printed on said support.

7. Apparatus according to claim 1 further comprising a housing within which said circuit means is situated, means detachably securing said antenna support to said housing, said housing comprising a housing sufficiently small to be placed with said antenna on the patient's body.

8. Apparatus according to claim 1 wherein, said low voltage power supply comprises means for supplying a voltage less than 50 volts.

9. Apparatus according to claim 1 wherein said support comprises a flexible support deformable to conform to the contour of the patient's body to which it is applied.

10. Apparatus according to claim 1 further comprising means matching said antenna to the output of said circuit means.

11. Apparatus according to claim 1, comprising a plurality of said antennas, said circuit means comprising a plurality of outputs, and for means connecting said antennas respectively to said outputs.

* * * * *